US006858038B2

(12) United States Patent
Heuser

(10) Patent No.: US 6,858,038 B2
(45) Date of Patent: Feb. 22, 2005

(54) STENT SYSTEM

(76) Inventor: Richard R. Heuser, 525 N. 18$^{th}$ St., Suite 504, Phoenix, AZ (US) 85006

( * ) Notice: Subject to any disclaimer, the term of this patent is extended or adjusted under 35 U.S.C. 154(b) by 0 days.

(21) Appl. No.: 10/177,816

(22) Filed: Jun. 21, 2002

(65) Prior Publication Data

US 2003/0236566 A1 Dec. 25, 2003

(51) Int. Cl.$^7$ .................................................. A61F 2/06
(52) U.S. Cl. ..................................... 623/1.35; 623/1.11
(58) Field of Search ................................. 623/1.1, 1.11, 623/1.12, 1.15, 1.16, 1.18, 1.19, 1.2, 1.35

(56) References Cited

U.S. PATENT DOCUMENTS

| | | | | |
|---|---|---|---|---|
| 5,984,955 A | * | 11/1999 | Wisselink | 623/1.35 |
| 6,124,523 A | * | 9/2000 | Banas et al. | 623/1.5 |
| 6,187,033 B1 | * | 2/2001 | Schmitt et al. | 623/1.35 |
| 6,325,826 B1 | * | 12/2001 | Vardi et al. | 623/1.35 |

OTHER PUBLICATIONS

Journal of the American College of Cardiology, vol. 38, No. 4: *Preliminary Results of Endovascular Abdominal Aortic Aneurysm Exclusion With the AneuRX Stent–Graft*. Oct. 2001.

* cited by examiner

*Primary Examiner*—Corrine McDermott
*Assistant Examiner*—Hieu Phan
(74) *Attorney, Agent, or Firm*—Kolisch Hartwell, P.C.

(57) ABSTRACT

A stent system is provided for percutaneous insertion in an artery of a main stent which includes at least one peripheral aperture defined through the stent wall. The stent system also includes a peripheral stent configured to be inserted into the peripheral aperture of the main stent. The peripheral stent extends, when inserted in the peripheral aperture, generally perpendicular to the longitudinal axis of the main stent. The stent system may further include a guidewire, insertable through the peripheral aperture, for maneuvering the main stent into place in the artery. The guidewire may be tapered toward its distal end. The stent system may also include a dilation device for dilating the peripheral stent within the peripheral aperture. The stent system may further include a tube inserted through the peripheral aperture of the main stent.

8 Claims, 6 Drawing Sheets

STENT SYSTEM

BACKGROUND

An aneurysm is an abnormal widening or expansion of a blood vessel, such as an artery, which occurs in a localized area of the artery and is typically the result of a weakening of the arterial wall caused by disease. The expansion is usually accompanied by a collection of fluid or clotted blood in the localized area. If the aneurysm is not treated, it typically will continue to expand, and may rupture, causing dangerous internal bleeding.

The most common locations for aneurysms are in the abdominal aorta, between the renal arteries and the split of the abdominal aorta into the left and right common iliac arteries, and in the upper legs, in the common iliac adjacent the take off of the internal iliac. Other vessels can be affected as well. The aneurysms in some cases involve only a single, main artery, but in other cases, one or more secondary arteries, branching from the main artery, are also weakened by disease and abnormally expanded. Such secondary arteries include the renal arteries and the superior mesenteric artery on the abdominal aorta, and the internal iliac off the common iliac artery.

Open surgery has been used to repair aneurysms, but, at least in part due to the morbidity rates associated with open surgery, percutaneous procedures are replacing it. The aneurysm is repaired in the percutaneous procedures by placing a covered stent in the affected main artery. However, such covered stents, particularly in the case of an aneurysm affecting one or more secondary arteries, such as the renal arteries or the internal iliac, do not adequately seal the aneurysm and are prone to leakage in the area adjacent the secondary arteries.

SUMMARY OF THE INVENTION

An embodiment of the present invention provides a stent system for repairing an aneurysm or associated or similar condition. The stent system includes a main stent, which may have a generally cylindrical wall, and at least one peripheral aperture through the wall. A peripheral stent is constructed to be installed in the peripheral aperture, extending therethrough, preferably generally perpendicular to a central longitudinal axis of the main stent. A guidewire may be combined with the main stent for guiding the stent through a human bodily fluid vessel, with the guidewire extending through the peripheral aperture of the main stent. The guidewire may also be used to position the peripheral stent.

A removable restraint may be installed around the main stent, particularly if the main stent is self-expanding, with a space in the restraint allowing access through the peripheral aperture of the main stent. If a dilation device is used in combination with the peripheral stent, it preferably includes a region of differential dilation for expanding one end of the peripheral stent more than an opposite end.

A tube may be inserted through the peripheral aperture of the main stent. The stents, main and/or peripheral, may be formed with an inner layer and an outer layer that provide flexible coverings, and a middle layer including a self-expanding structure.

DETAILED DESCRIPTION OF THE PREFERRED EMBODIMENTS

Figure 1:
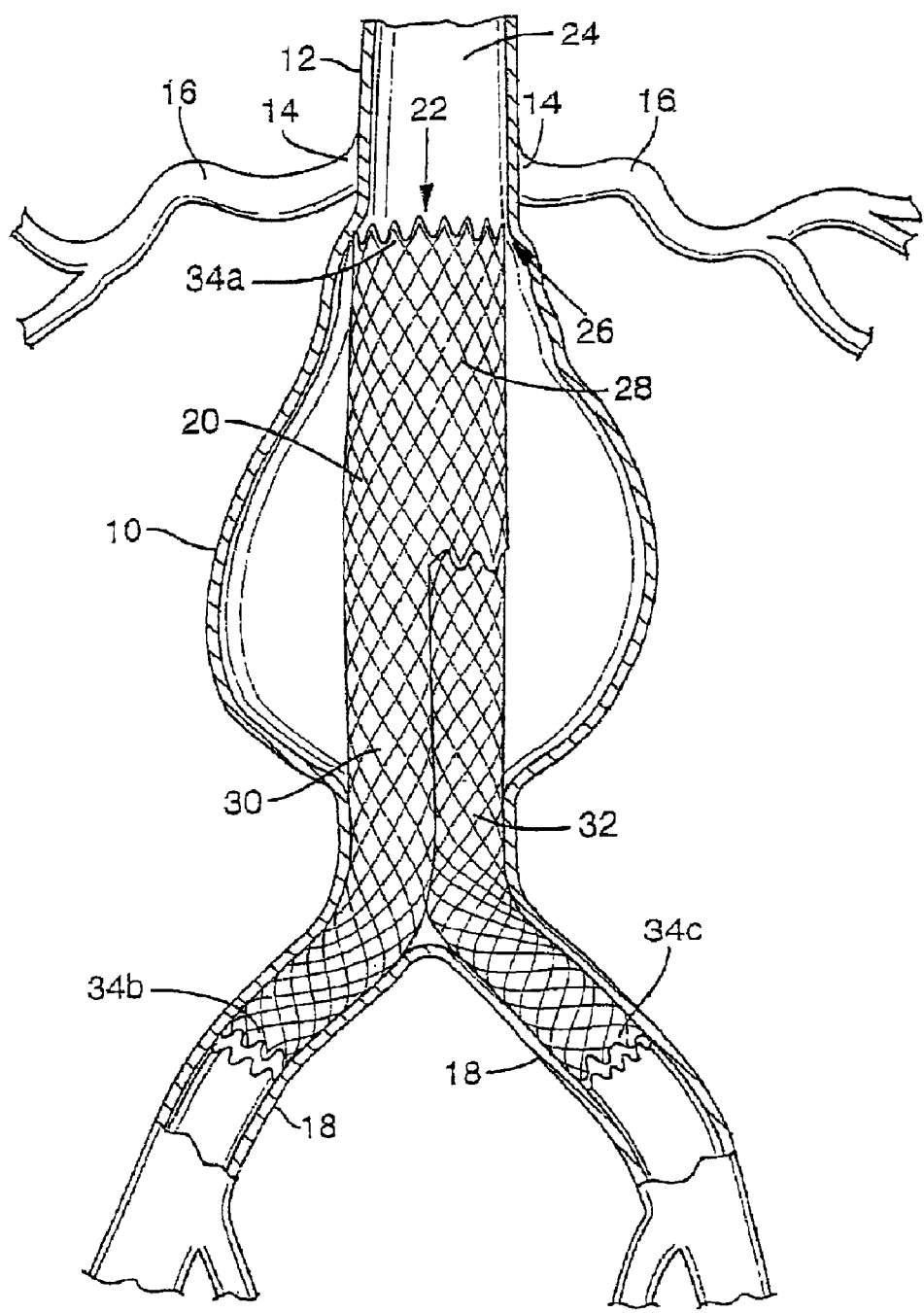
FIG. 1 is a cross-sectional view of an aneurysm in an abdominal aorta between the renal arteries and the common iliacs, showing a prior art endoluminal graft installed to extend from below the renal arteries into the left and right common iliacs, above the take-offs of the internal iliacs.

The prior art device for treating an aneurysm 10 in an abdominal aorta 12 is illustrated in FIG. 1. Aneurysm 10 extends from the takeoffs 14 of the renal arteries 16 down to the split of the abdominal aorta 12 into the left and right common iliacs 18. A standard endoluminal graft 20 has been installed in the aneurysm in an attempt to provide a flow path 22 for blood 24 past the aneurysm and into the common iliacs. However, because of the involvement in the aneurysm of the renal arteries, graft 20 has not sealed off the aneurysm and blood may leak into the aneurysm at gap 26.

Nonetheless, graft 20 cannot be extended up the aorta further without blocking the renal arteries. The prior art graft provides no way to treat an aneurysm while maintaining open the takeoffs of dependent arteries from the main artery being treated. Occluding the dependent arteries causes several problems, including allowing the aneurysm to continue filling with blood from collaterals supplying the dependent artery. For an aneurysm on the abdominal aorta, the result can include loss of kidney function, bowel ischemia, perineal ischemia, and impotence.

Prior art graft 20 includes a wide-channel upper portion 28 above an integral narrow-channel portion 30 extending down into one common iliac, and a separately attached narrow-channel portion 32 extending into the other common iliac. Each of the three portions of graft 20 is constructed of a generally solid and continuous wall 34a–c wrapped into a cylindrical shape to define a channel with two open ends. The two narrow-channel portions are coupled, one integrally, the other attached during surgery, to one of the open ends of the wide-channel portion. Each of the portions defines a longitudinal axis, and all three of the axes run generally parallel to one another.

Figure 2:
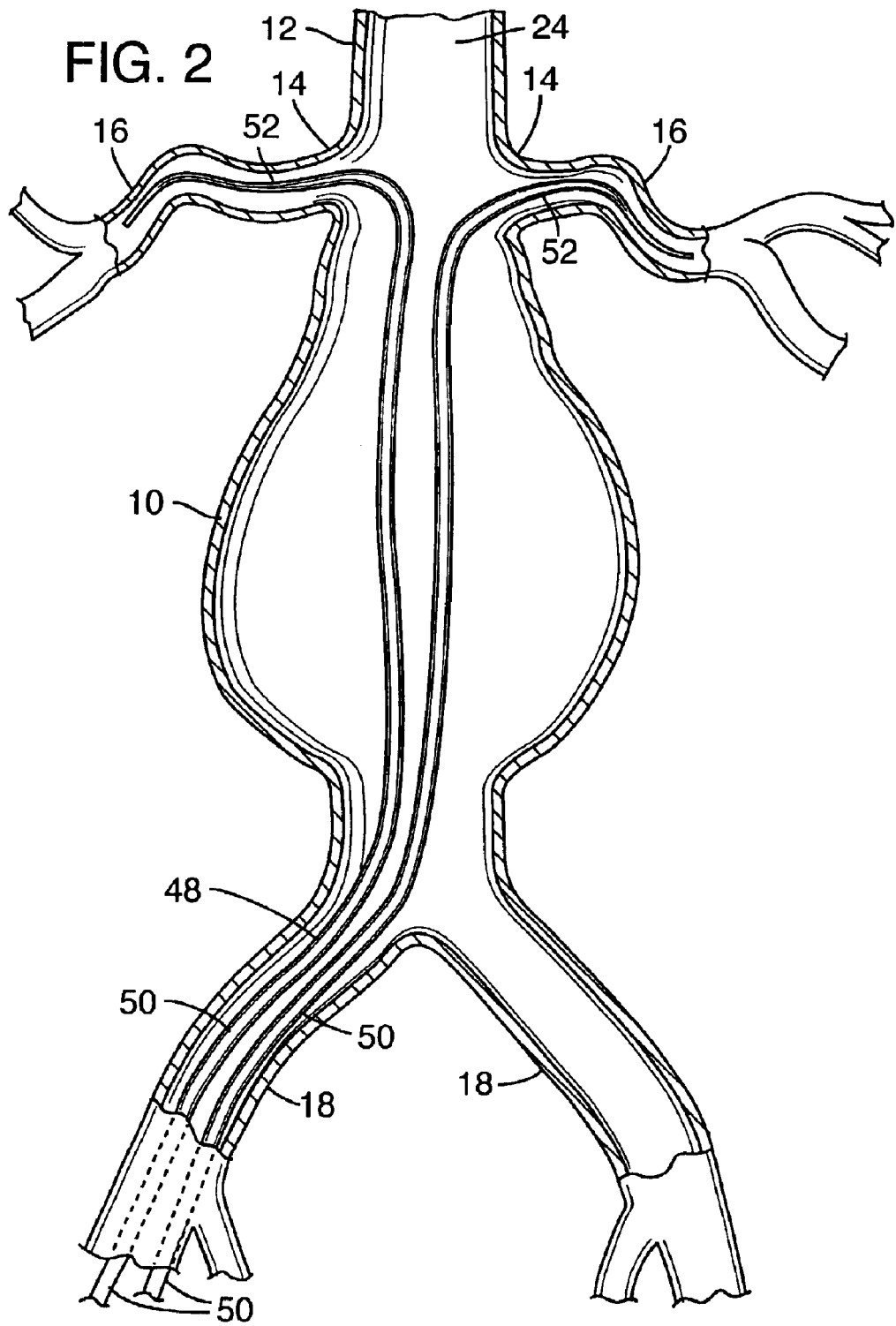
FIG. 2 is a cross-sectional view of the abdominal aorta, shown without the endoluminal graft of FIG. 1, with a pair of guidewires with tapering distal ends, in accordance with an embodiment of the present invention, inserted through one common iliac and the abdominal aorta, with each of the distal ends extending into one of the renal arteries.

The embodiments of the present invention for a stent system shown in FIGS. 2–9 can be used either independently or in combination with the graft shown in FIG. 1, typically to treat an aneurysm, but also to treat a torn artery. As shown in FIG. 2, two guidewires 48, in accordance with an embodiment of the present invention, can be percutaneously inserted into a common iliac 18 and guided up through the abdominal aorta 12, past graft 20, if such is installed (see FIG. 3), and into the renal arteries 16. Guidewire 48 typically includes a main body 50, preferably about 0.064" in diameter, to provide a sufficiently stiff portion for guiding through the arteries.

Guidewire 48 includes a distal portion 52, and the diameter of guidewire 48 preferably tapers in distal portion 52, preferably tapering over a length of about 8 to 10 cm, typically to about half the diameter of the main body, and preferably to a final diameter of about 0.036". The dimensions of these features of the guidewire will vary depending on the materials used, the particular artery and percutaneous procedure under consideration, and other factors. Guidewire 48 is typically formed of nitinol, at least in the main body portion. The distal portion is preferably formed of a soft and/or hydrophilic material, so as to promote entry of the distal portion into the renal arteries, or other dependent artery.

Figure 3:
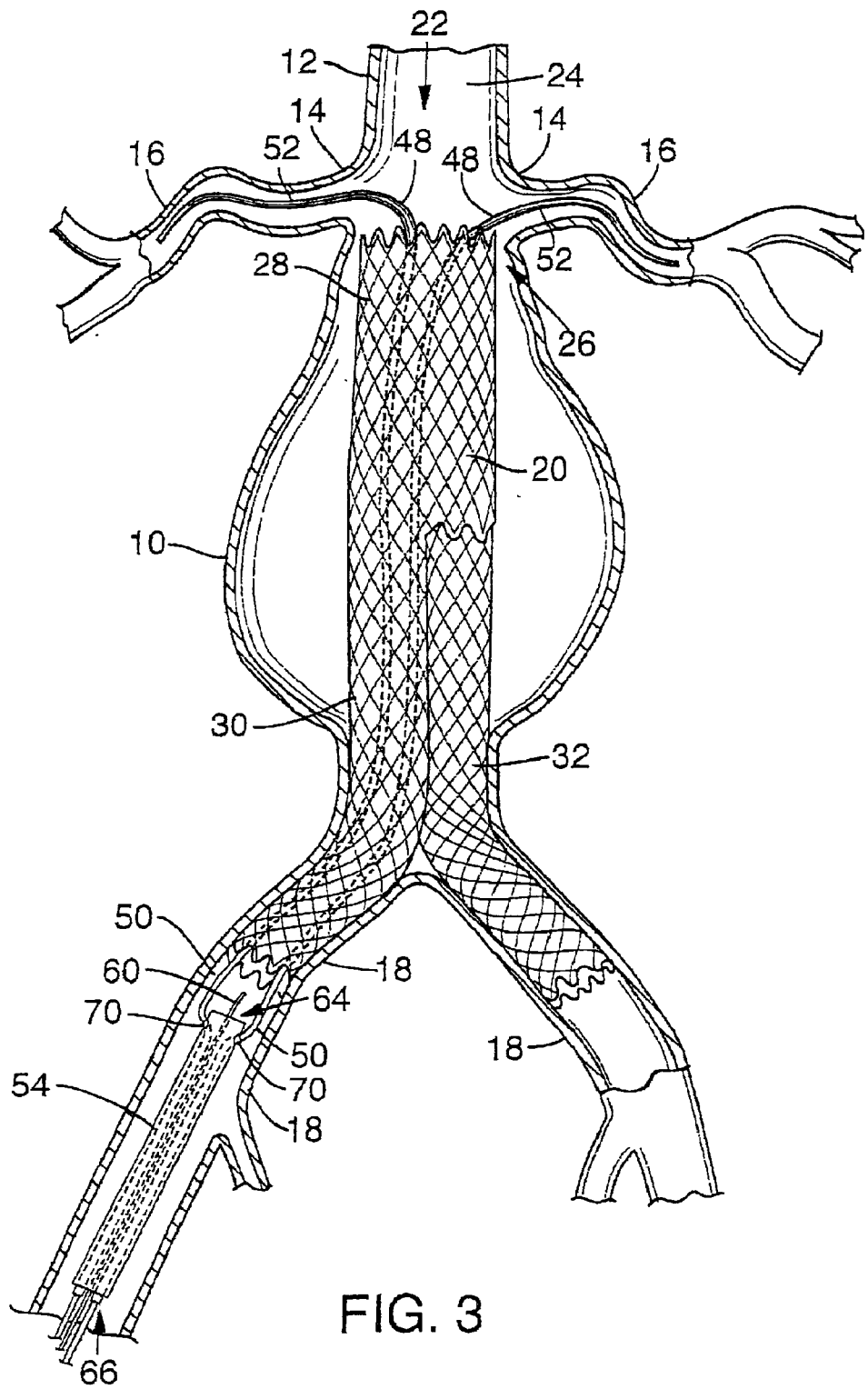
FIG. 3 is a cross-sectional view, as in FIG. 2, shown with the endoluminal graft of FIG. 1, with a main stent, in accordance with an embodiment of the present invention inserted into the common iliac and being pushed up the two guidewires, which extend through two peripheral apertures in the stent, the main stent is compressed and is carried on a catheter, and the stent includes a pair of tubes inserted into the peripheral apertures so that the guidewires extend through the tubes.
Figure 4:
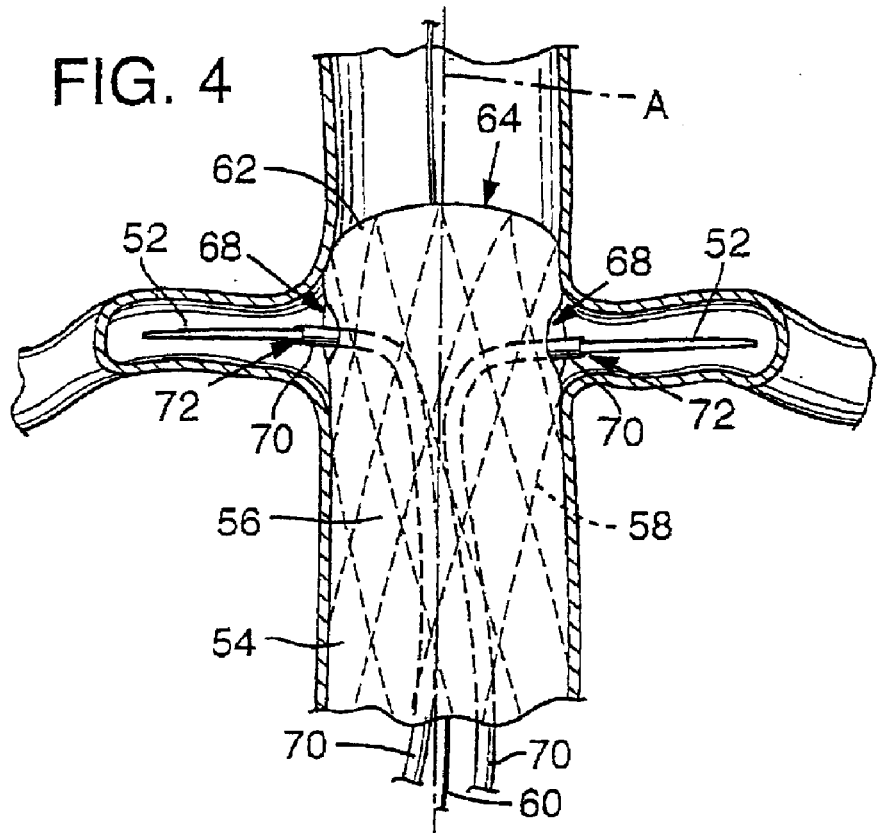
FIG. 4 is a cross-sectional, close-up view of the embodiment shown in FIG. 3, showing the main stent in place and expanded in the abdominal aorta at a position and orientation where the peripheral apertures of the main stent face the renal arteries, and with the tubes in the peripheral apertures still in position.

With guidewires 48 in place in the artery, and with distal portions 52 extending into the dependent arteries that are desired to be maintained open, a main stent 54 can slide along guidewires 48, as shown in FIGS. 3 and 4, for accurate, aligned placement at the dependent arteries. Main stent 54 may be of balloon-expandable or self-expandable type, and typically includes a flexible covering 56 and mesh structure 58. Main stent 54 may be fixedly, removably mounted on another guidewire, such as balloon catheter 60, to slide stent 54 along the guidewires 48. The mesh structure 58 of stent 54 may be designed to provide for self-expansion of stent 54, or not, in accordance with known stent designs.

Figure 5:
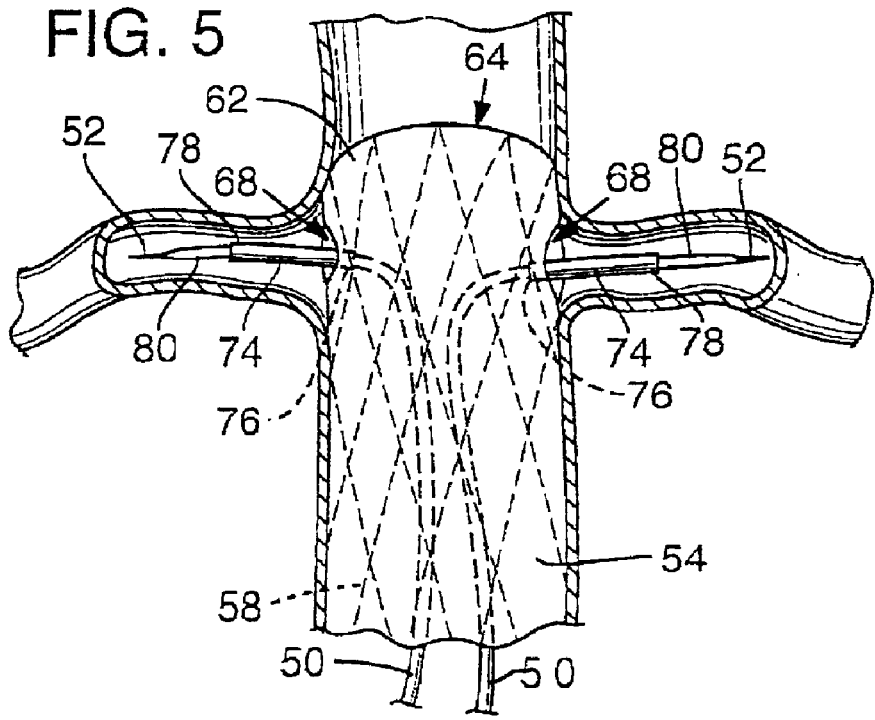
FIG. 5 is a cross-sectional view, as in FIG. 4, showing the main stent with the tubes withdrawn from the peripheral apertures, and with two peripheral stents inserted through the peripheral apertures of the main stent and into the renal arteries, and with the peripheral stents still compressed.

As best seen in FIGS. 4 and 5, main stent 54 is constructed of a wall 62 in a generally cylindrical shape and defining a central longitudinal axis A, and typically constructed of flexible covering 56 and mesh structure 58. Main stent 54 has two main openings 64, 66 opposite one another. Main stent 54 includes two peripheral apertures 68 defined through wall 62. The two peripheral apertures 68, best seen in FIGS. 3–6, are designed to be aligned with a patient's renal arteries, and the number and configuration of the apertures will depend on the application intended for the stent.

Two tubes 70, preferably formed of a relatively non-compressible, slick material, for example an appropriately selected type of Silastic® material, as made by Dow Corning, may be installed in main stent 54 and through apertures 68, with a portion extending outside of main stent 54. Tubes 70 include a channel 72 defined therethrough. Guidewires 48 are inserted through tubes 70 and through apertures 68, so that stent 54 can slide along guidewires 48, pushed along by balloon catheter 60 or other mechanism. Tubes 70 may be coupled to catheter 60 to fix stent 54 in place on catheter 60 during insertion of stent 54.

As shown in FIG. 3, with main stent 54 in a compressed condition, apertures 68 are tight around tubes 70, and tubes 70 maintain apertures 68 open and promote sliding movement of stent 54 along guidewires 48, although apertures 68 may alternately be designed to accommodate sliding movement along guidewires 48 without tubes 70. Guidewires 48, once inserted into the dependent arteries, promote accurate longitudinal and rotational positioning of stent 54, so that peripheral apertures 68 face the dependent arteries.

With main stent 54 in place, adjacent the aneurysm and aligned with the arteries desired to be maintained open, stent 54 can be expanded. If stent 54 is self-expanding, a removable restraint, such as a membrane or sheath is withdrawn from the stent, typically by the catheter used to push stent 54 into place. Removal of the restraint allows the self-expanding structure in the stent to expand and fix the stent in place in the artery. If stent 54 is balloon-expandable, balloon catheter 60 is activated to expand the stent and fix it in place in the artery. The end result of either of these operations is shown in FIG. 4, where it will also be seen that apertures 68 have expanded and no longer tightly encompass tubes 70.

With main stent 54 expanded in place in the artery, tubes 70 may be withdrawn along guidewires 48, e.g., by withdrawing balloon catheter 60 if coupled to tubes 70 as described above. Peripheral stents 74 may be slid along guidewires 48 and through expanded stent 54 to a desired position at the dependent arteries, as shown in FIG. 5. Peripheral stent 74, which preferably is a covered, balloon-expandable stent, includes a first end 76 and a second end 78. Each peripheral stent 74 is preferably positioned with first end 76 remaining within the main stent, and the second end 78 extending out of main stent 54 and into the dependent artery. Peripheral stents 74 extend generally perpendicular to longitudinal axis A of main stent 54. Alternatively, stent 54 may be installed in the artery with the peripheral apertures aligned with the dependent arteries and no peripheral stent.

Peripheral stents 74 may be moved into place, for example, by inserting a catheter 80 with a central lumen over guidewire 48 and sliding the catheter along guidewire 48. Under some circumstances, it may be desirable to only partially withdraw tubes 70 from main stent 54, requiring that each catheter 80 and each peripheral stent 74, in its compressed condition, fit through tube 70. Alternatively, tubes 70 may be completely withdrawn from guidewires 48 before catheters 80 are fitted over the guidewires.

Figure 6:
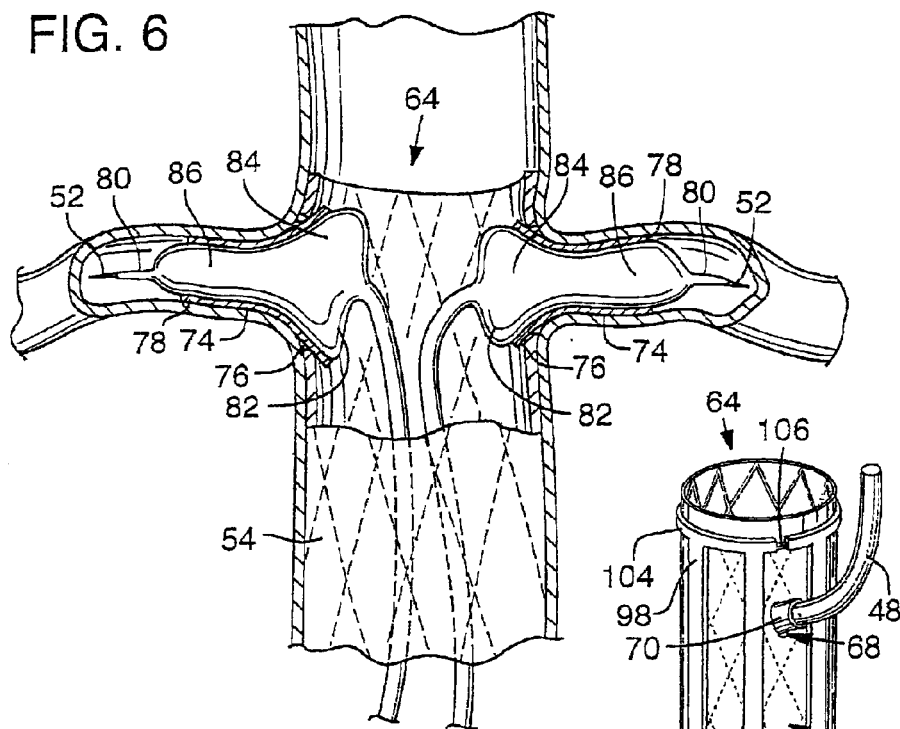
FIG. 6 is a cross-sectional view, as in FIG. 5, with the main stent, shown in partial cross-section, and the peripheral stents shown in cross-section, and dilation devices completing the differential dilation or trumpeting of the peripheral stents.

Catheter 80 may also provide a dilation device, such as a balloon 82, best seen in FIG. 6. Preferably, balloon 82 has two differentially-expanding regions 84, 86, so that first end 76 of peripheral stent 74 is expanded more than second end 78. First end 76 preferably is trumpeted or increasingly expanded toward the first end. Alternatively the differential expansion may be accomplished by separate balloons or sequential differential expansion of a single balloon, or by other means. The differential expansion is believed to more firmly fix peripheral stent 74 in place in peripheral aperture 68 and to provide a funnel-shaped conduit to promote blood flow into the dependent arteries.

Figure 7:
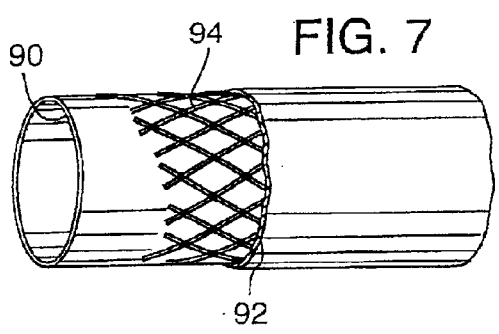
FIG. 7 is an isometric, partial cutaway view of a stent, in accordance with an embodiment of the present invention, showing an inner layer, providing a flexible covering, a middle layer providing a self-expanding structure, and an outer layer providing a flexible covering.

A preferred embodiment for any of the main stent or the peripheral stents is shown in FIG. 7. The stent includes an inner layer 90 providing a flexible covering, as with flexible covering 56, an outer layer 92 providing a second flexible covering, and a middle layer 94 between the inner and outer layers. Middle layer 94 includes a compressible, typically self-expanding structure, as with mesh structure 58. The inner and outer layers are preferably formed of PTFE, and the middle layer of nitinol.

Figure 8:
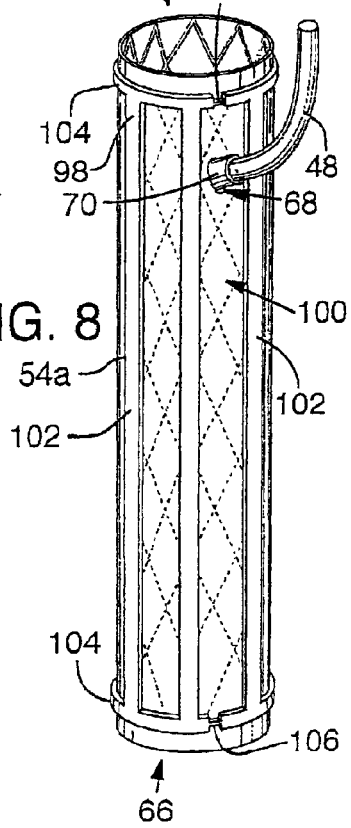
FIG. 8 is an isometric view of a self-expanding stent, in accordance with an embodiment of the present invention, showing a removable restraint with a space to allow the tube to extend through one of the peripheral apertures, and including breakaway points on the restraint to facilitate removal past the tubes.

FIG. 8 shows an embodiment for a self-expanding stent 54a, in accordance with the present invention, which typically will be used as the main stent and includes one or more peripheral apertures and tubes or guidewires extending therethrough. Stent 54a includes a removable restraint 98 disposed around the generally cylindrical wall of the stent body to hold stent 54a in a compressed condition. Restraint 98 preferably includes a space 100 adjacent peripheral aperture 68 and tube 70 allowing access through the peripheral aperture, and a second space or spaces at other peripheral apertures (not shown), if the stent includes such. In the embodiment shown in FIG. 8, space 100 is provided between strips 102 that interconnect two bands 104, one at each end of restraint 98, but any configuration providing a space for the peripheral apertures may be used. Bands 104 typically include a breakaway point, such as narrowed portion 106, to allow the band to break at the tube 70 or guidewire 48 extending through the aperture as the restraint is withdrawn from stent 54a.

Figure 9:
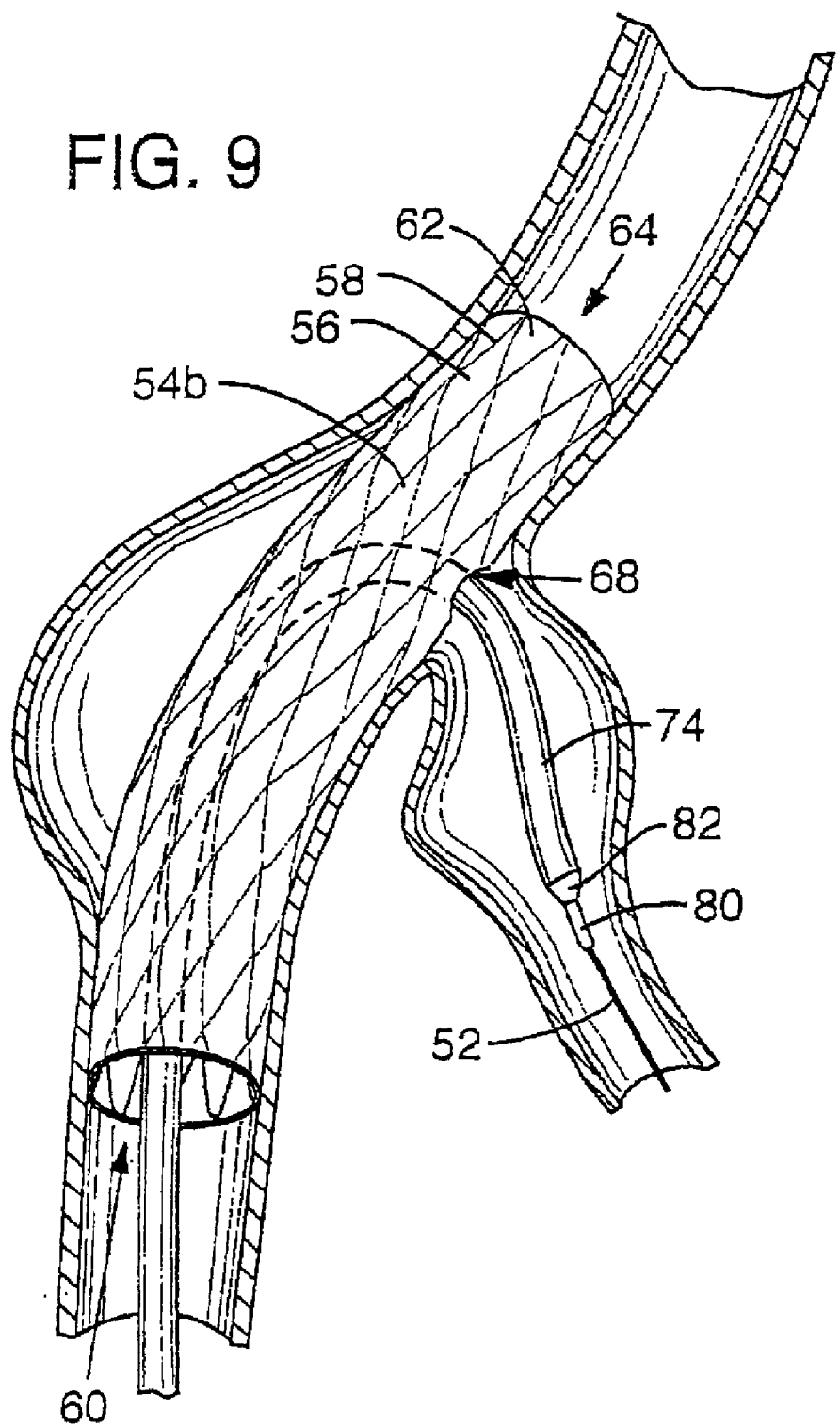
FIG. 9 is a cross-sectional view of an aneurysm in an artery with a single side artery involved in the aneurysm and showing an embodiment of the present invention with a single peripheral aperture, and a tube inserted in the peripheral aperture, a guidewire extending through the tube and into the side artery, and a balloon catheter carrying a peripheral stent on the guidewire.

FIG. 9 shows an embodiment for a stent system, in accordance with the present invention, and for use in repairing an aneurysm involving the takeoff of the internal iliac. This system may be used independently or in conjunction with the graft shown in FIG. 1. The system includes main stent 54b expanded in place at the aneurysm with a single peripheral aperture 68 aligned with the internal iliac. Guidewire 48 had been initially inserted along the external iliac, with distal portion 52 extending into the internal iliac, and stent 54b was slid along guidewire 48, and then expanded. After expansion of main stent 54b, catheter 80 was slid along guidewire 48, with peripheral stent 74 disposed on balloon 82 on catheter 80. Stent 74 is positioned to be expanded into place, once tubes 70 are withdrawn. In general, the structure of this single-peripheral-aperture system is the same as that for the system shown in the preceding figures. It will be understood that these systems illustrate that the invention includes placing a stent system in any artery at any dependent artery or arteries to maintain open flow.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. No single feature, function, element or property of the disclosed embodiments is essential to all of the disclosed inventions. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower or equal in scope to the original claims, are also included within the subject matter of the inventions of the present disclosure.

I claim:

1. A stent system for installation in a human bodily fluid vessel, the stent system comprising:

a main stent including a generally cylindrical wall defining a central longitudinal axis, and having a first main opening and an opposite second main opening, the stent including at least one peripheral aperture defined through the wall;

a tube removably installed in, and extending through the peripheral aperture, the tube preventing closure of the peripheral aperture, the tube including a channel extending therethrough, the channel configured to receive a guidewire, the tube fixed in place for movement of the main stent relative to the guidewire and configured to be removed from the main stent as part of the installation of the stent system in the human bodily vessel; and a peripheral stent configured to be inserted into the peripheral aperture of the main stent after removal of the tube, the peripheral stent extending, when inserted in the peripheral aperture, generally perpendicular to the longitudinal axis of the main stent.

2. The stent system of claim 1 wherein the main stent includes a second peripheral aperture defined through the wall, and further comprising a second peripheral stent configured to be inserted in the second peripheral aperture.

3. The stent system of claim 2 wherein the second peripheral stent, when inserted in the second peripheral aperture, extends generally perpendicular to the longitudinal axis of the main stent.

4. The stent system of claim 1 wherein the tube is formed substantially of a slick material selected to allow the main stent to slide along the guidewire.

5. The stent system of claim 1 wherein the main stent includes a second peripheral aperture defined through the wall, and further comprising a second peripheral stent configured to be inserted in the second peripheral aperture, and also comprising a second tube inserted through the second peripheral aperture, the second tube including a channel extending therethrough, the channel configured to receive a second guidewire, the second tube configured to be removed from the main stent as part of the installation in the human bodily vessel.

6. The stent system of claim 1 wherein the main stent includes a removable restraint disposed around the wall of the main stent.

7. The stent system of claim 6 wherein the removable restraint includes a space adjacent the peripheral aperture and the tube extends through the space.

8. The stent system of claim 7 wherein the removable restraint is configured to breakaway adjacent the tube as the restraint is removed from the main stent.

* * * * *